(12) United States Patent
Zhu (10) Patent No.: US 11,197,505 B2
(45) Date of Patent: Dec. 14, 2021

(54) LOAD AND STERILIZATION COMBINATION CONTROL CIRCUIT

(71) Applicant: Shenzhen KangerTech Technology Co., Ltd., Shenzhen (CN)

(72) Inventor: Xiaochun Zhu, Shenzhen (CN)

(73) Assignee: SHENZHEN KANGERTECH TECHNOLOGY CO., LTD., Shenzhen (CN)

( * ) Notice: Subject to any disclaimer, the term of this patent is extended or adjusted under 35 U.S.C. 154(b) by 52 days.

(21) Appl. No.: 16/896,194

(22) Filed: Jun. 8, 2020

(65) Prior Publication Data

US 2021/0120879 A1 Apr. 29, 2021

(30) Foreign Application Priority Data

Oct. 23, 2019 (CN) .......................... 201911012177.2

(51) Int. Cl.
| | |
|---|---|
| *A24F 40/50* | (2020.01) |
| *A24F 40/85* | (2020.01) |
| *A24F 40/90* | (2020.01) |
| *A61L 2/10* | (2006.01) |
| *A61L 2/26* | (2006.01) |
| *H02J 7/00* | (2006.01) |

(52) U.S. Cl.
CPC .............. *A24F 40/50* (2020.01); *A24F 40/85* (2020.01); *A24F 40/90* (2020.01); *A61L 2/10* (2013.01); *A61L 2/26* (2013.01); *H02J 7/007* (2013.01); *H02J 7/0029* (2013.01); *A61L 2202/11* (2013.01); *A61L 2202/14* (2013.01)

(58) Field of Classification Search
None
See application file for complete search history.

(56) References Cited

U.S. PATENT DOCUMENTS

| 6,090,346 A | * | 7/2000 | Rose ......................... A61L 2/02 |
| | | | 422/128 |
| 6,201,354 B1 | * | 3/2001 | Kokubo ..................... B41J 2/32 |
| | | | 315/194 |
| 2003/0113246 A1 | * | 6/2003 | Saitou ..................... B01D 53/04 |
| | | | 422/305 |
| 2004/0166037 A1 | * | 8/2004 | Youdell .................... A61L 9/205 |
| | | | 422/186.3 |
| 2014/0042341 A1 | * | 2/2014 | Park ....................... A45D 29/00 |
| | | | 250/492.1 |

\* cited by examiner

*Primary Examiner* — Andrew Smyth (57) ABSTRACT

A load and sterilization combination control circuit arranged on a suction device includes a main control unit, a battery management unit, a load output unit, a load detection circuit and an ultraviolet sterilization circuit including an operation switch and an enabled switch connected with the operation switch in series and the main control unit. The load detection unit and the enabled switch are conducted to externally output. When a load of the suction device applied on the load output unit is detected by the main control unit via the load, detection circuit, the operation switch is configured to perform on-off control on the entire ultraviolet sterilization circuit after the enabled switch is turned on. The present disclosure can avoid waste electricity due to misoperation by performing a linkage control thereof and the ultraviolet sterilization circuit can work normally only after by connecting with the load and closing the operation switch.

16 Claims, 6 Drawing Sheets

LOAD AND STERILIZATION COMBINATION CONTROL CIRCUIT

BACKGROUND

1. Technical Field

The present disclosure generally relates to electronic cigarettes field, and especially relates to a load and sterilization combination control circuit used in a suction device such as an electronic cigarette.

2. Description of Related Art

As an electronic device that works by simulating a conventional cigarette, an electronic heat suction device is configured to atomize smoke oil containing nicotine, propylene glycol, glycerin, essence and other ingredients stored in an atomizer through a heating wire, so as to simulate the smoke produced by smoking, which can not only simulate a taste of smoking via essence, but also simultaneously satisfy the nicotine intake demand needed by smokers.

In order to enhance functions of the electronic heat suction device, some suction devices on the market include a body and a power supply shell designed independently. The body generally includes an atomizer and a host, and the power supply shell includes a chamber for receiving the body therein, a power supply member and a sterilization member. When the body is received in the power supply shell, it can not only directly supply power or charge the body, but also sterilize a nozzle of the atomizer received in the body.

However, a sterilization circuit and a power supply circuit of the conventional suction device are separately controlled. In this way, the sterilization circuit can also be opened when the body isn't put into the power supply shell, thus resulting in the waste of electric energy caused by misoperation.

SUMMARY

The technical problems to be solved: in view of the shortcomings of the related art, the present disclosure relates to a load and sterilization combination control circuit which can avoid the waste of electric energy due to misoperation.

The technical solution adopted for solving technical problems of the present disclosure is:

A load and sterilization combination control circuit arranged on a suction device includes:

a main control unit, a battery management unit, a load output unit, a load detection circuit and an ultraviolet sterilization circuit;

an input end of the battery management unit connected with an external power supply, and an output end of the battery management unit connected with the main control unit and an input end of the load output unit so as to apply power supply for the main control unit, the load output unit, the load detection circuit and the ultraviolet sterilization circuit; the load output unit configured to output the power supply input from the battery management unit to the ultraviolet sterilization circuit and the load of the suction device; the load detection circuit connected between the battery management unit and the load of the suction device, and both the load output unit and the load detection circuit connected with the main control unit;

the ultraviolet sterilization circuit including an operation switch and an enabled switch connected with the operation switch in series, and connected with the main control unit;

the main control unit configured to conduct the load output unit and send an external output signal to the load output unit, and then conduct the enabled switch, when the load of the suction device applied on the load output unit is detected by the main control unit via the load detection circuit; and wherein the operation switch is configured to perform on-off control on the entire ultraviolet sterilization circuit after the enabled switch is turned on.

Wherein the load output unit includes an enabled control circuit connected with the main control unit, and a boosted circuit; an input end of the enabled control circuit connected with the output end of the battery management unit, and an output end of the enabled control circuit connected with an input end of the boosted circuit; the boosted circuit including two output ends, with one output end thereof connecting with an input end of the ultraviolet sterilization circuit, and the other output end thereof connecting with the load of the suction device;

the ultraviolet sterilization circuit including the operation switch, an ultraviolet sterilization lamp and the enabled switch connected in series in turn;

the main control unit configured to controllably conduct the enabled control circuit and the enabled switch so as to connect with the boosted circuit, when the load of the suction device applied on the load output unit is detected by the main control unit via the load detection circuit and the operation switch configured to perform on-off control on the entire ultraviolet sterilization circuit to light up or turn off the ultraviolet sterilization lamp after the enabled switch is turned on.

Wherein the battery management unit includes a charging interface, a charging circuit, a battery, a battery protection circuit and a voltage regulator circuit;

the charging circuit connected with the charging interface and the battery protection circuit, the battery protection circuit connected with the battery, both the charging circuit and the battery protection circuit simultaneously connected with the load output unit and the voltage regulator circuit, and the voltage regulator circuit connected with the main control unit;

the charging interface connected with the external power supply and configured to output an output voltage to the charging circuit, and then the charging circuit configured to charge the battery connected with the battery protection circuit, the battery protection circuit configured to output a voltage to the load output unit and the voltage regulator circuit, the voltage regulator circuit configured to output a stable voltage to the main control unit.

Wherein the main control unit includes a main control chip U1 including an output enabled pin OUT_EN1, an LED1 pin and a load detection pin F_CHK;

the output enabled pin OUT_EN1 connected with the enabled control circuit of the load output unit, the load detection pin F_CHK connected with the load detection circuit, and the LED1 pin connected with the enabled switch of the ultraviolet sterilization circuit and configured to control on and off of the enabled switch.

Wherein the enabled control circuit includes a field-effect tube Q1, a triode Q2 controllably connected with the field-effect tube Q1 and the output enabled pin OUT_EN1, the output end of the battery management unit connected with both the field-effect tube Q1 and the triode Q2;

the boosted circuit including a boosted chip U2 with an input end thereof connecting with the field-effect tube Q1, and an output end thereof connecting with an ultraviolet output end VOUT and a load output end, the ultraviolet output end VOUT connected with the input end of the ultraviolet sterilization circuit; the load output end including a load anode contact point and a load cathode contact point connected with the ultraviolet output end VOUT in parallel, both the load anode contact point and the load cathode contact point conducted in series when the load is applied, and the load cathode contact point, connected with the load detection circuit and then grounded.

Wherein the load output unit further includes a voltage sampling circuit and a short-circuit detection circuit;

the voltage sampling circuit arranged at the output end of the boosted chip U2 and configured to sample a voltage to compare with a reference voltage of the boosted chip U2;

the short-circuit detection circuit connected with the load cathode contact point and a short-circuit detection pin CHA_CHK of the main control chip U1.

Wherein the main control chip U1 further includes an enabled pin OUT_EN2 connected with the short-circuit detection circuit so as to control turn-on and turn-off of the short-circuit detection circuit.

Wherein the ultraviolet sterilization circuit further includes a load input end, and a current-limiting resistance, and the operation switch includes a contact switch positive set and a contact switch negative set, the ultraviolet lamp is an ultraviolet LED, the enabled switch is a triode Q5, all the load input end, the current-limiting resistance, the contact switch positive set, the ultraviolet LED, the contact switch negative set and the triode Q5 connected in series in turn to cooperatively form a series circuit thereof; and wherein the triode Q5 is controllably connected with the LED1 pin, and the contact switch positive set and the contact switch negative set are connected with or shut off the whole series circuit.

Wherein the load and sterilization combination control circuit further includes a displaying screen connected with the main control unit, and the battery management unit is connected with the displaying screen to apply power supply for the displaying screen.

Wherein the load of the suction device includes a heating wire, a suction control circuit and a pneumatic induction switch electrically connected with the suction control circuit, an input end of the suction control circuit connected with an output end of the load output unit, and an output end of the suction control circuit connected with the heating wire.

Wherein the output end of battery management unit is connected with a second pin of the field-effect tube Q1 and is connected with a resistance R2; a first pin of the field-effect tube Q1 connected with a resistance R4, and then, together with the resistance R2, connected with a third pin of the triode Q2, a second pin of the triode Q2 being grounded, and the third pin of the triode Q2 connected in parallel with a resistance R6 and a resistance R7, an opposite end of the resistance R6 being grounded and an opposite end of the resistance R7 including a contact connected with the output enabled pin OUT_EN1 of the main control chip U1.

Wherein a third pin of the field effect tube Q1 is connected with a VCC pin of the boosted chip U2 for input, and also connected with an EN pin and an OC pin of the boosted chip U2, an LX pin of the boosted chip U2 connected with the ultraviolet output end VOUT and the load anode contact point through a diode D1, and the load cathode contact point connected with resistances R10, R11 in series and then grounded; an F_CHK contact arranged between the resistance R10 and the resistance R11 is connected with the load detection pin F_CHK of the main control chip U1, Wherein the output end of the battery management unit is connected with a resistance R1 in parallel when the output end of the battery management unit is connected with the field-effect tube Q1 and the triode Q2; the resistance R1 connected with the load anode contact point; all the resistance R1, the load anode contact point, the load cathode contact point, the resistance R10, the load detection pin F_CHK and the resistance R11 cooperatively formed the load detection circuit.

Wherein the voltage sampling circuit includes a resistance R3 connected in parallel with the ultraviolet output end VOUT and the load anode contact point, and a resistance R5 connected in series with the resistance R3; an FB pin of the boosted chip U2 connected between the resistance R3 and the resistance R5, a voltage, first sampled by the resistance R3 and the resistance R5, and then compared with a voltage of an FB reference point of the boosted chip U2 so as to adjust the output voltage of the boosted chip U2.

Wherein the short-circuit detection circuit includes a field-effect tube Q3 and a resistance R17, a second pin of the field-effect tube Q3 connected with the resistance R15 and the resistance R17, an opposite end of the resistance R15 connected with a capacitor C9 and including a CHA_CHK contact connected with the short-circuit detection pin CHA_CHK of the main control chip U1, an opposite end of the resistance R17 being grounded, an opposite end of the capacitor C9 being grounded, and a third pin of the field-effect tube Q3 connected with the load cathode contact point.

Wherein a first pin of the field-effect tube Q3 is connected with a resistance R12, an opposite end of the resistance R12 including an OUT_EN2 contact connected with the enabled pin OUT_EN2 of the main control chip U1; when the main control chip U1 is configured to conduct the field-effect tube Q3 through the enabled pin OUT_EN2, the short-circuit detection circuit is in a working state.

The present disclosure provides the advantages as below.

The structure of the present disclosure is provided the main control unit, the battery management unit, the load output unit, the load detection circuit and the ultraviolet sterilization circuit, and the ultraviolet sterilization circuit is set in linkage with the load detection circuit and the load output unit. That is, when the load of the suction device applied on the load output unit is detected by the main control unit via the load detection circuit, the load output unit is turned on to supply power to the ultraviolet sterilization circuit and to conduct the enabled switch of the ultraviolet sterilization circuit. After that, the ultraviolet sterilization circuit can be normally controlled by the operation switch set thereon. That is, the ultraviolet sterilization circuit can work normally only after the ultraviolet sterilization circuit is connected with the load of the suction device, and the operation switch is closed, which can avoid the waste of electric energy caused by misoperation.

DETAILED DESCRIPTION

The disclosure is illustrated by way of example and not by way of limitation in the figures of the accompanying drawings, in which like reference numerals indicate similar elements.

Figure 1:
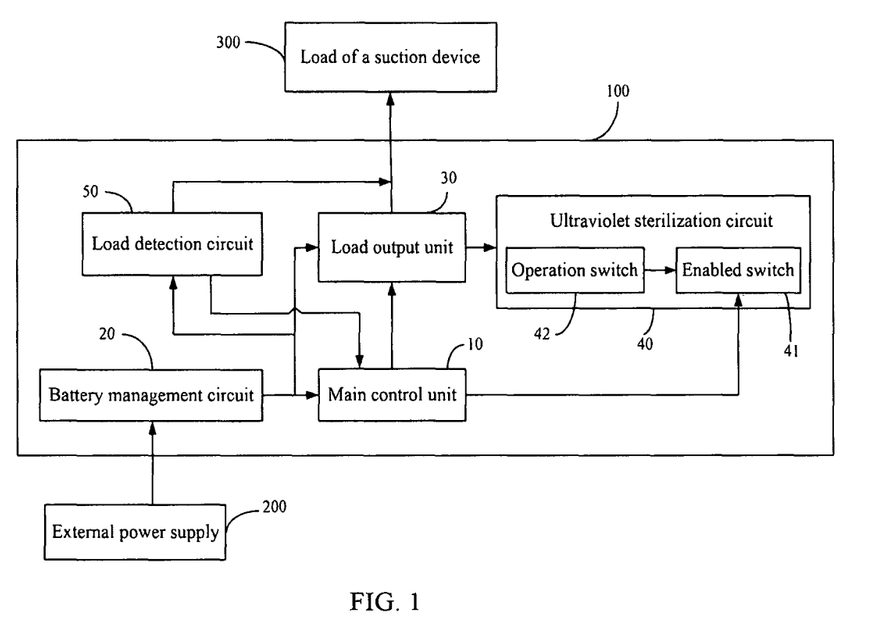
FIG. 1 is a schematic diagram of a load and sterilization combination control circuit in accordance with a first embodiment of the present disclosure.
Figure 2:
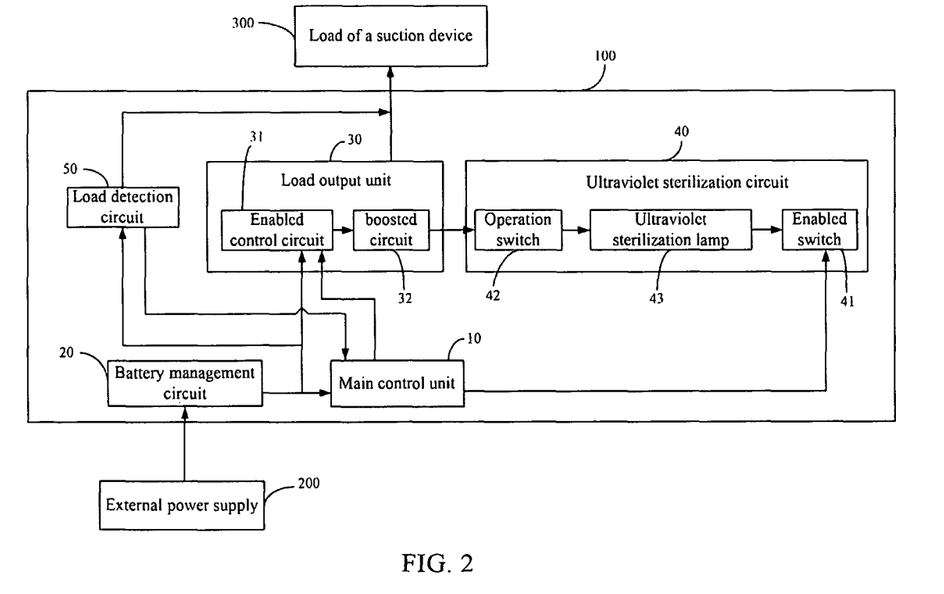
FIG. 2 is a schematic diagram of a load and sterilization combination control circuit in accordance with a second embodiment of the present disclosure.

Referring to FIGS. 1-2, the load and sterilization combination control circuit 100 in accordance with an embodiment of the present disclosure is arranged on a suction device. In an embodiment of the present disclosure, the suction device includes an electronic cigarette body and a power supply housing which includes a receiving room for receiving the electronic cigarette body therein. The power supply housing can be configured to supply power or charge the electronic cigarette body. The load and sterilization combination control circuit 100 of the present disclosure is received in the power supply housing.

The load and sterilization combination control circuit 100 includes a main control unit 10, a battery management unit 20, a load output unit 30, a load detection circuit 50 and an ultraviolet sterilization circuit 40.

An input end of the battery management unit 20 is connected with an external power supply 200, and an output end of the battery management unit 20 is connected with the main control unit 10 and an input end of the load output unit 30 so as to apply power supply for the main control unit 10, the load output unit 30, the load detection circuit 50 and the ultraviolet sterilization circuit 40. The load output unit 30 is configured to output the power supply input from the battery management unit 20 to the ultraviolet sterilization circuit 40 and the load 300 of the suction device. The load detection circuit 50 is connected between the battery management unit 20 and the load 300 of the suction device, and both the load output unit 30 and the load detection circuit 50 are connected with the main control unit 10. The load 300 of the suction device can be a heating wire of an electronic cigarette or, an assembly combined by a heating wire in the electronic cigarette, a battery and a control circuit.

The battery management unit 20 includes a battery therein so that the battery management unit 20 can charge the battery after the load and sterilization combination control circuit 100 is connected with the external power supply 200, and then supply power for the main control unit 10, the load output unit 30 and the load detection circuit 50. After that, the load output unit 30 is configured to supply power for the load 300 of the suction device and the ultraviolet sterilization circuit 40. The load detection circuit 50 is configured to feedback a load signal to the main control unit 10 to determine whether the load of the electronic cigarette body is connected with the load and sterilization combination control circuit 100. At the same time, the main control unit 10 is connected with the load output unit 30 to control an output of the load output unit 30.

The ultraviolet sterilization circuit 40 includes an operation switch 42 and an enabled switch 41 connected with the operation switch 42 in series, and connected with the main control unit 10.

The main control unit 10 is configured to conduct the load output unit 30 and send an external output signal to the load output unit 30, and then conduct the enabled switch 41, when the load 300 of the suction device applied on the load output unit 30 is detected by the main control unit 10 via the load detection circuit 50. The operation switch 42 is configured to perform on-off control on the entire ultraviolet sterilization circuit 40 after the enabled switch 41 is turned on.

It can be understood that the operation switch 42 of the present disclosure can be a mechanical push switch, a touch switch, a flip type contact switch, etc. The ultraviolet sterilization circuit 40 includes components emitting ultraviolet light, such as an ultraviolet LED, etc.

After the load detection circuit 50 detected that the load 300 of the suction device is connected, the main control unit 10 is configured to conduct the load output unit 30 and send an external output signal to the load output unit 30, and further conduct the enabled switch 41 of the ultraviolet sterilization circuit 40. In this way, the ultraviolet sterilization circuit 40, the load detection circuit 50 and the load output unit 30 are cooperatively to form a linkage control circuit. The ultraviolet sterilization circuit 40 can work normally only when the load 300 is connected and the operation switch 42 is closed. And, when the load 300 of the suction device isn't connected, the enabled switch 41 of the ultraviolet sterilization circuit 40 can't be connected because the load output unit 30 isn't connected with the external output, so even if the operation switch 42 is closed, the ultraviolet sterilization circuit 40 still can't work. Or, after the load 300 of the suction device is connected, and both the load output unit 30 and the enabled switch 41 are conducted, but if the operation switch 42 isn't closed at this time, the ultraviolet sterilization circuit 40 still can't work, which can avoid a defect in the prior art that the ultraviolet sterilization circuit 40 can be opened separately when the load 300 of the suction device isn't connected, that is, it can avoid the defect that the ultraviolet sterilization circuit 40 can be opened separately when the electronic cigarette body isn't received in the power supply housing, thus avoiding an operation error and the waste of electric energy.

When the control circuit 100 of the present disclosure is not initially connected with the load 300, the load output unit 30 is disconnected, and the load detection circuit 50 is configured to provide power supply through the battery management unit 20 for detections.

Furthermore, referring to FIG. 2, the load output unit 30 includes an enabled control circuit 31 connected with the main control unit 10, and a boosted circuit 32. An input end of the enabled control circuit 31 is connected with the output end of the battery management unit 20, and an output end of the enabled control circuit 31 is connected with an input end of the boosted circuit 32. The boosted circuit 32 includes two output ends, with one output end thereof connecting with an input end of the ultraviolet sterilization circuit 40, and the other output end thereof connecting with the load 300 of the suction device.

The boosted circuit 32 is configured to boost the power supply provided by the battery management unit 20. Generally, a voltage of the battery in the battery management unit 20 is about 3.7v, while a working voltage of the load 300 of the suction device such as the battery of the electronic cigarette or the heating wire and the ultraviolet lamp is about 5V, therefore, the power supply of the battery management unit 20 is needed to be boosted. The enabled control circuit 31 is controlled by the main control unit 10, which is further configured to control an external output voltage of the boosted circuit 32.

The ultraviolet sterilization circuit 40 includes the operation switch 42, an ultraviolet sterilization lamp 43 and the enabled switch 41 connected in series in turn.

The main control unit 10 is configured to controllably conduct the enabled control circuit 31 and the enabled switch 41 so as to connect with the boosted circuit 32, when the load 300 of the suction device applied on the load output unit 30 is detected by the main control unit 10 via the load detection circuit 50. The operation switch 42 is configured to perform on-off control on the entire ultraviolet sterilization circuit 40 to light up or turn off the ultraviolet sterilization lamp 43 after the enabled switch 41 is turned on.

That is, the main control unit 10 is configured to identify a signal fed back from the load detection circuit 50. When the load 300 of the suction device is connected with the output end of the load output unit 30, the main control unit 10 can control the enabled control circuit 31 to conduct so that the power supply input from the battery management unit 20 can enter the boosted circuit 32, and then output to the load 300 of the suction device and the ultraviolet sterilization circuit 40 after the power supply is boosted by the boosted circuit 32. At this time, the power supply can be provided for the ultraviolet sterilization circuit 40, and the enabled switch 41 of the ultraviolet sterilization circuit 40 is also conducted under the control of the main control unit 10. However, at this time, the whole ultraviolet sterilization circuit 40 is not fully connected, furthermore, the whole ultraviolet sterilization circuit 40 can be conducted by manually closing the operation switch 42, so that a current can flow through the ultraviolet sterilization lamp 43 to promote the ultraviolet sterilization lamp 43 work normally so as to emit ultraviolet radiation for sterilizing the nozzle of the electronic cigarette body in the suction device.

Figure 3:
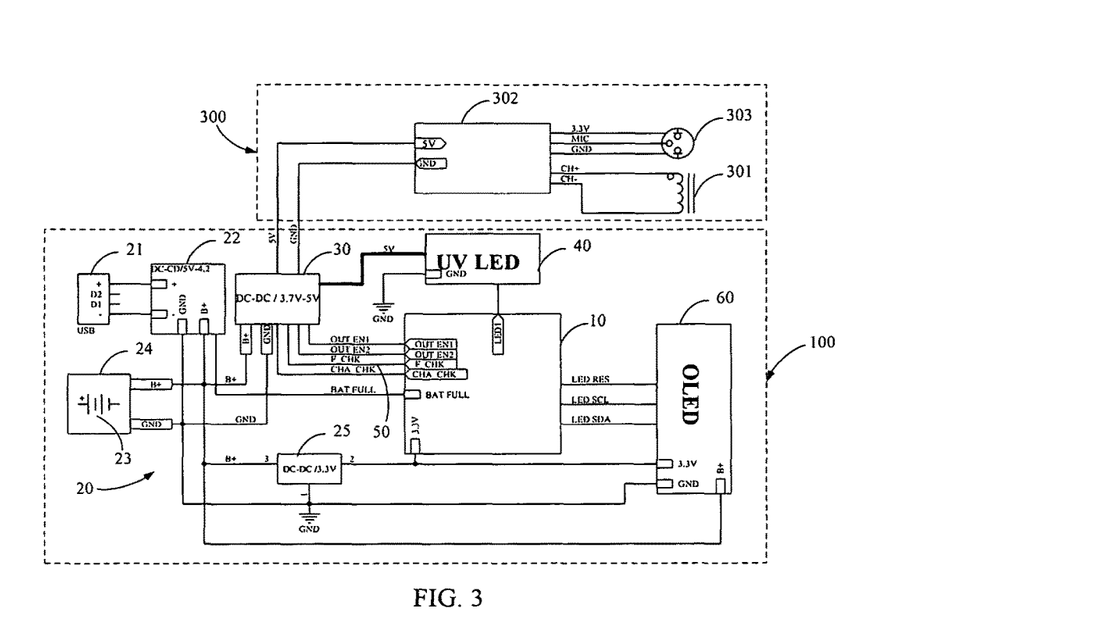
FIG. 3 is a schematic diagram of a load and sterilization combination control circuit in accordance with a third embodiment of the present disclosure.
Figure 4:
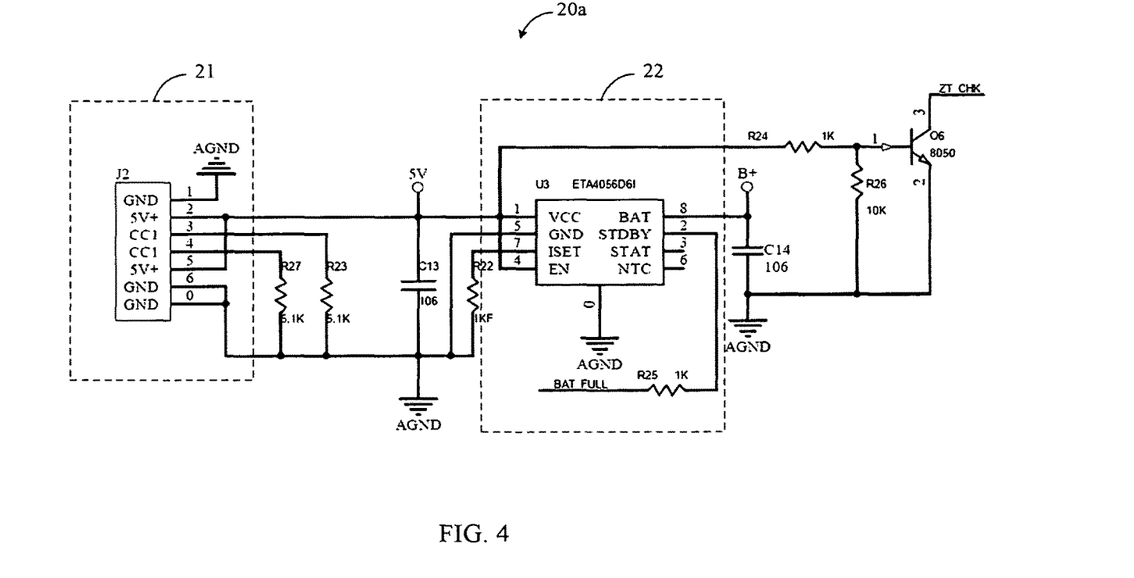
FIG. 4 is a schematic diagram of a first circuit of a battery management unit of the load and sterilization combination control circuit of the present disclosure.
Figure 5:
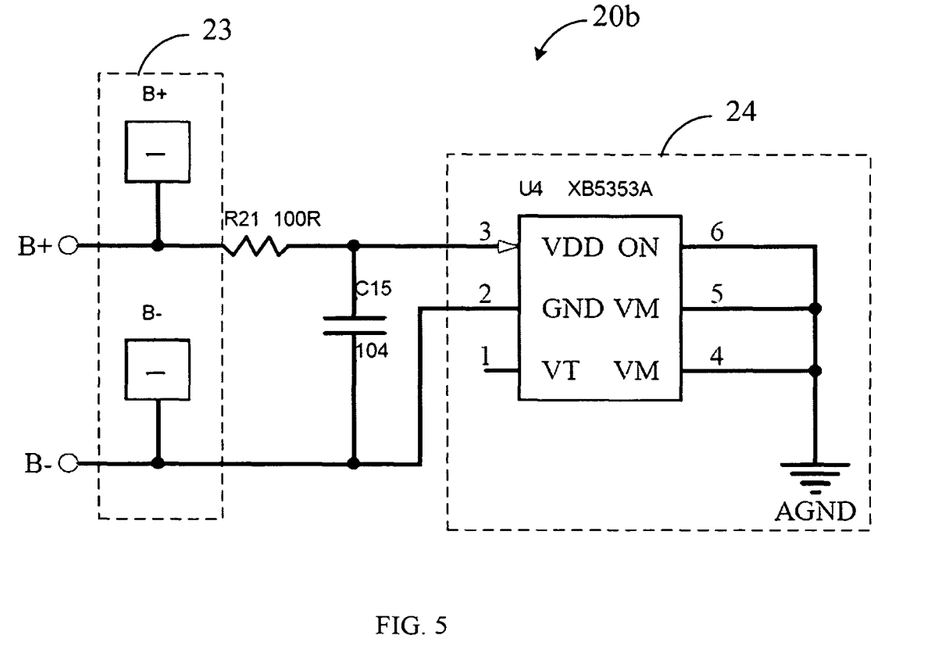
FIG. 5 is similar to FIG. 4, but shown a second circuit of the battery management unit.

Referring to FIGS. 3-5, the battery management unit 20 includes a charging interface 21, a charging circuit 22, a battery 23, a battery protection circuit 24 and a voltage regulator circuit 25.

The charging circuit 22 is connected with the charging interface 21 and the battery protection circuit 24, and the battery protection circuit 24 is also connected with the battery 23. Both the charging circuit 22 and the battery protection circuit 24 are simultaneously connected with the load output unit 30 and the voltage regulator circuit 25, and the voltage regulator circuit 25 is connected with the main control unit 10.

The charging interface 21 is connected with the external power supply 200 and configured to output an output voltage to the charging circuit 22, and then the charging circuit 22 is configured to charge the battery 23 connected with the battery protection circuit 24. The battery protection circuit 24 is configured to output a voltage to the load output unit 30 and the voltage regulator circuit 25. The voltage regulator circuit 25 is configured to output a stable voltage to the main control unit 10.

A first circuit 20a of the battery management unit 20 of the present disclosure is shown in FIG. 4. The first circuit 20a includes the charging interface 21 and the charging circuit 22. The charging circuit 22 of the present disclosure is a chip U3 with a model ETA4056D6I to charge the battery 23. A second pin of the chip U3 is connected with a pin BAT_FULL of the main control unit 10 representing of charging state signals. When the battery 23 is fully charged, the second pin of the chip U3 is configured to output a level signal to the main control unit 10, and then the main control unit 10 is configured to show a full state indication and shut off charging the battery 23.

Referring to FIG. 5 it is shown a second circuit 20b of the battery management unit 20 of the present disclosure. The second circuit 20b includes the battery 23 and the battery protection circuit 24. The battery protection circuit 24 of the present disclosure is a chip U4 with a model XB5353A to protect the battery 23 and prevent the battery 23 from being over-charge, being over-discharge and, being over-current. Furthermore, an end B+ and an end B− are respectively represented an input end and an output end of charging and discharging the battery.

The voltage regulator circuit 25 (not shown) of the present disclosure is designed as a chip with a model ME6209A33M3G to connect with the main control unit 10.

Referring to FIG. 3, the main control unit 10 of the present disclosure includes a main control chip U1 including an output enabled pin OUT_EN1, an LED1 pin and a load detection pin F_CHK.

Furthermore, the output enabled pin OUT_EN1 is connected with the enabled control circuit 31 of the load output unit 30, and the load detection pin F_CHK is connected with the load detection circuit 50. The LED1 pin is connected with the enabled switch 41 of the ultraviolet sterilization circuit 40 and configured to control on and off of the enabled switch 41. The main control chip U1 is configured to control the on-off of the enabled control circuit 31 through the output enabled pin OUT_EN1 so as to control the external output of the entire load output unit 30, and further control the on-off of the enabled switch 41 through the LED1 pin.

Figure 6:
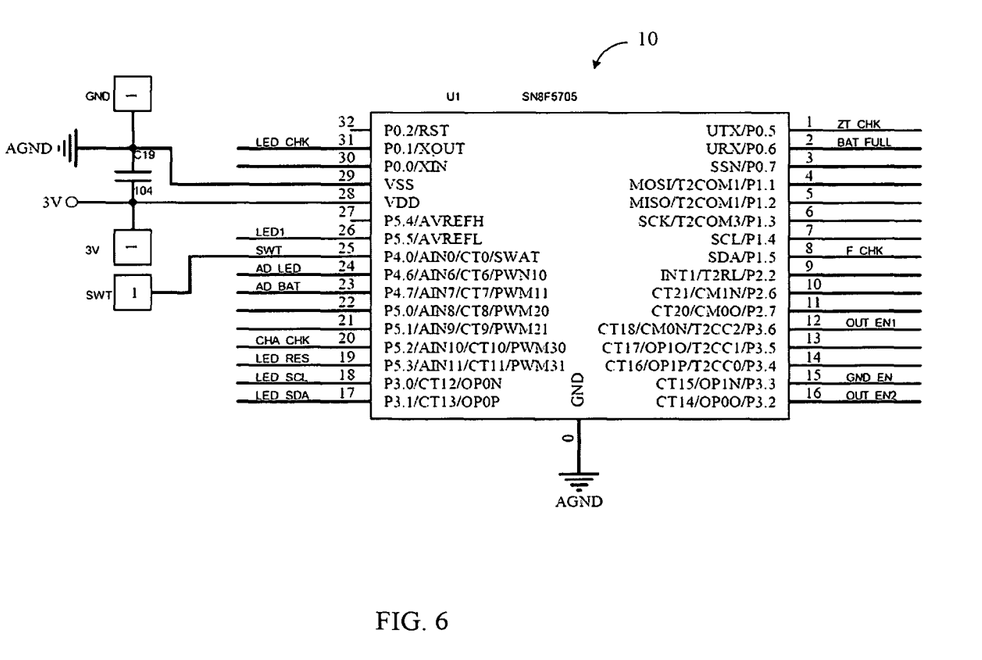
FIG. 6 is a schematic diagram of a main control unit of the load and sterilization combination control circuit of the present disclosure.
Figure 7:
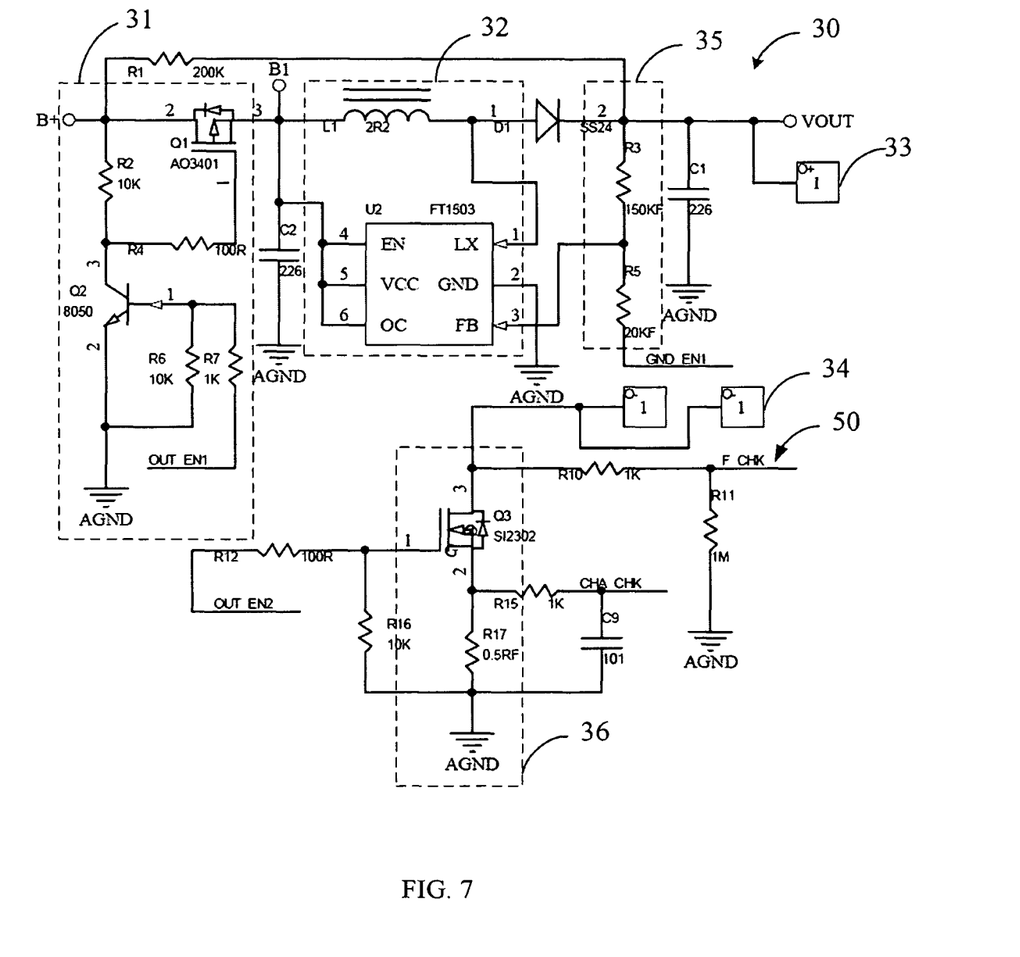
FIG. 7 is a schematic diagram of a load output unit and a load detection circuit of the load and sterilization combination control circuit of the present disclosure.

Specifically, referring, to FIG. 6 and FIG. 7, a model of the main, control chip U1 is SN8F5705. The enabled control circuit 31 of the present disclosure includes a field-effect tube Q1, a triode Q2 controllably connected with the field-effect tube Q1 and the output enabled pin OUT_EN1. The output end of the battery management unit 20 is connected with both the field-effect tube Q1 and the triode Q2. Referring to FIG. 7, the output end B+ of the battery management unit 20 is connected with a second pin of the field-effect tube Q1 and is connected with a resistance R2. A first pin of the field-effect tube Q1 is connected with a resistance R4, and then, together with the resistance R2, connected with a third pin of the triode Q2. A second pin of the triode Q2 is grounded, and the first pin of the triode Q2 is connected in parallel with a resistance R6 and a resistance R7. An opposite end of the resistance R6 is grounded and an opposite end of the resistance R7 includes a contact OUT_EN1 connected with the output enabled pin OUT_EN1 of the main control chip U1.

The boosted circuit 32 includes a boosted chip U2 with an input end thereof connecting with the field-effect tube Q1, and an output end thereof connecting with an ultraviolet output end VOUT and a load output end. The ultraviolet output end VOUT is connected with the input end of the ultraviolet sterilization circuit 40. The load output end includes a load anode contact point 33 and a load cathode contact point 34 connected with the ultraviolet output end VOUT in parallel. Both the load anode contact point 33 and the load cathode contact point 34 are conducted in series when the load 300 is connected, and the load cathode contact point 34 is connected with the load detection circuit 50 and then is grounded.

Referring to FIG. 7, a model of the boosted chip U1 is FT1503. A third pin of the field-effect tube Q1 is connected with a VCC pin of the boosted chip U2 for input, and also connected with an EN pin and an OC pin of the boosted chip U2. An LX pin of the boosted chip U2 is connected with the ultraviolet output end VOUT and the load anode contact point 33 through a diode D1, and the load cathode contact point 34 is connected with resistances R10, R11 in series and then is grounded. An F_CHK contact arranged between the resistance R10 and the resistance R11 is connected with the load detection pin F_CHK of the main control chip U1.

The output end B+ of the battery management unit 20 is connected with a resistance R1 in parallel when the output end B+ of the battery management unit 20 is connected with the field-effect tube Q1 and the triode Q2. The resistance R1 is also connected with the load anode contact point 33. All the resistance R1 the load anode contact point 33, the load cathode contact point 34, the resistance R10, the load detection pin F_CHK and the resistance R11 are cooperatively formed the load detection circuit.

When the load 300 isn't connected between the load anode contact point 33 and the load cathode contact point 34, none path is formed in the load detection circuit 50 and none loop is formed between the resistances R1, R10 and the resistance R11, a voltage at the F_CHK contact is zero. After such voltage signal is transmitted to the main control unit 10 through the load detection pin F_CHK, the main control unit 10 is configured to determine that none load is connected. And then, the main control unit 10 is further configured to send a disconnection signal to the enabled control circuit 31 through the output enabled pin OUT_EN1, so that both the triode Q2 and the field-effect tube Q1 are disconnected and the power supply of the boosted chip U2 is shut off. In this way, none output voltage is applied on the ultraviolet output end VOUT and the load anode contact point 33, thereby the entire control circuit 100 is worked in a power-saving mode.

When the load 300 is connected between the load anode contact point 33 and the load cathode contact point 34, so that the load anode contact point 33 and the load cathode contact point 34 are connected with each other. In this way, a path is formed in the load detection circuit 50 and a loop is formed between the resistances R1, R10 and the resistance R11. At this time, a voltage at the F_CHK contact between the resistor R10 and the resistor R11 is increased. After such voltage signal is transmitted to the main control unit 10 through the load detection pin F_CHK, the main control unit 10 is configured to determine that the load 300 is connected. And then, the main control unit 10 is further configured to send a connection signal to the enabled control circuit 31 through the output enabled pin OUT_EN1, so that the triode Q2 is connected and then the field-effect tube Q1 is also connected, thus a power supply is applied for the boosted circuit U2. Therefore, the booster chip U2 is entered a normal working mode to provide a stable voltage for the ultraviolet output terminal VOUT and the load anode contact point 33.

Furthermore, the load output unit 30 further includes a voltage sampling circuit 35 and a short-circuit detection circuit 36. The voltage sampling circuit 35 is arranged at the output end of the boosted chip U2 and configured to sample a voltage to compare with a reference voltage of the boosted chip U2. Referring to FIG. 7, the voltage sampling circuit 35 includes a resistance R3 connected in parallel with both the ultraviolet output end VOUT and the load anode contact point 33, and a resistance R5 connected in series with the resistance R3. An FB pin of the boosted chip U2 is connected between the resistance R3 and the resistance R5, a voltage is first sampled by the resistance R3 and the resistance R5, and then compared with a voltage of an FB reference point of the boosted chip U2 so as to adjust the output voltage of the boosted chip U2.

The short-circuit detection circuit 36 is connected with the load cathode contact point 34 and a short-circuit detection pin CHA_CHK of the main control chip U1. Referring to FIG. 7, the short-circuit detection circuit 36 includes a field-effect tube Q3 and a resistance R17. A third pin of the field-effect tube Q3 is connected with the load cathode contact point 34, a second pin of the field-effect tube Q3 is connected with the resistance R15 and the resistance R17. An opposite end of the resistance R15 is connected with a capacitor C9 and includes a CHA_CHHK contact connected with the short-circuit detection pin CHA_CHK of the main control chip U1, an opposite end of the resistance R17 is grounded, and an opposite end of the capacitor C9 is also grounded.

When the connected load is short-circuited, a current passing through the field-effect tube Q3 and the resistance R17 is too great so that the voltage between the resistance R17 and the field-effect tube Q3 is increased. At this time, a voltage at the CHA_CHK contact between the resistance R15 and the capacitor C9 is also increased, so that such signal is fed back to the main control unit 10 through the short-circuit detection pin CHA_CHK. The main control unit 10 can control the enabled control circuit 31 by the output enabled pin OUT_EN1 to close the field-effect tube Q1 and shut off the output of the boosted chip U2 after the signal is received by the main control unit 10, thereby a protective effect can be achieved.

Furthermore, the main control chip U1 further includes an enabled pin OUT_EN2 connected with the short-circuit detection circuit 36 so as to control turn-on and turn-off of the short-circuit detection circuit 36. Referring to FIG. 7, a first pin of the field-effect tube Q3 is connected with a resistance R12, an opposite end of the resistance R12 includes an OUT_EN2 contact connected with the enabled pin OUT_EN2 of the main control chip U1. When the main control chip U1 is configured to conduct the field-effect tube Q3 through the enabled pin OUT_EN2, the whole short-circuit detection circuit 36 is in a working state.

Figure 8:
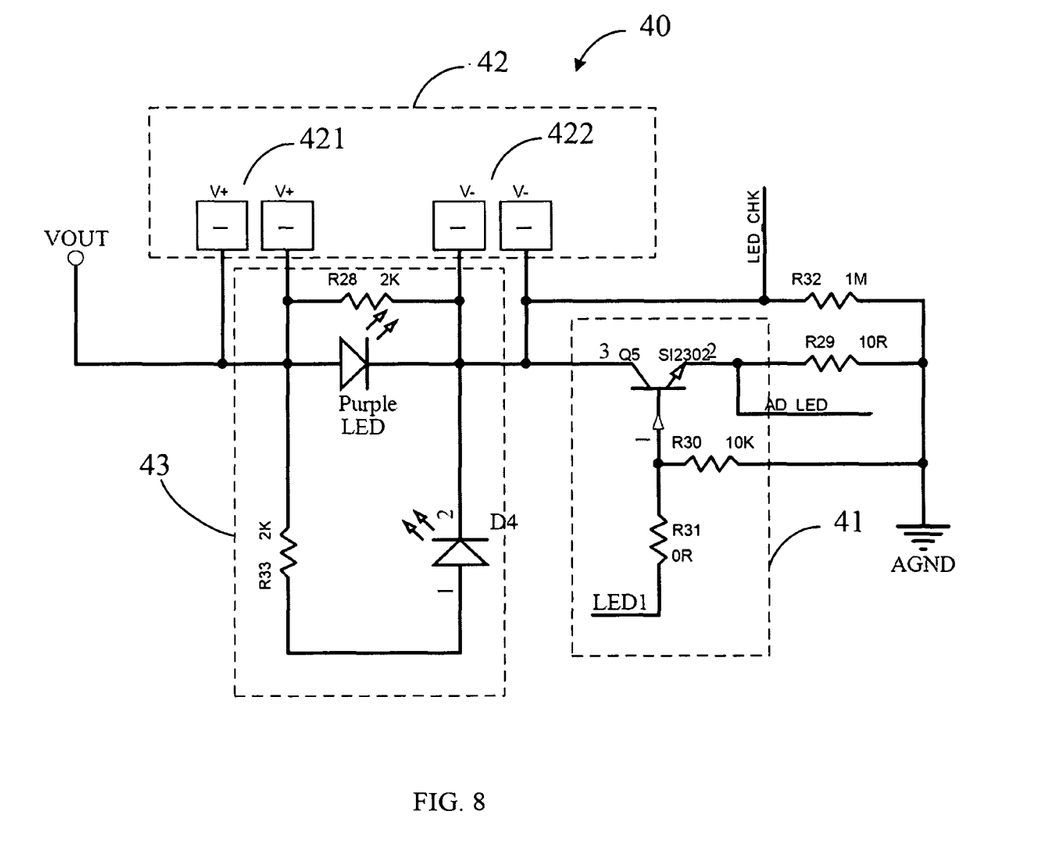
FIG. 8 is a schematic diagram of an ultraviolet sterilization circuit of the load and sterilization combination control circuit of the present disclosure.

Referring to FIG. 8, the ultraviolet sterilization circuit 40 further includes a load input end and a current-limiting resistance R29, and the operation switch 42 includes a contact switch positive set 421 and a contact switch negative set 422. The ultraviolet lamp 43 is an ultraviolet LED, and the enabled switch 41 is a triode Q5. All the load input end, the contact switch positive set 421, the ultraviolet LED 43, the contact switch negative set 422, the triode Q5 and the current-limiting resistance R29 are connected in series in turn to cooperatively faun a series circuit thereof.

The triode Q5 is controllably connected with the LED1 pin of the main control chip U1, and the contact switch positive set 421 and the contact switch negative set 422 are connected with or shut off the whole series circuit.

The load input end of the ultraviolet sterilization circuit 40 is connected with the ultraviolet output end VOUT so as to obtain a power supply. In an embodiment of the present disclosure, the power supply housing of the suction device includes a cover formed on the top thereof, and the contact switch positive set 421 and the contact switch negative set 422 are two pairs of contacts arranged on the cover and the power supply housing, respectively. That is, the contact switch positive set 421 includes two contacts respectively arranged on the cover and the power supply housing, and so does the contact switch negative set 422. When the cover is opened, the two contacts of the contact switch positive set 421 are separated and disconnected, so does two contacts of the contact switch negative set 422. While, when the cover is closed, the two contacts of the contact switch positive set 421 are connected and conducted, so does two contacts of the contact switch negative set 422. Referring to FIG. 8, when the main control unit 10 determined that the load 300 is connected through the load detection pin F_CHK, the main control unit 10 is configured to conduct the load output unit 30 through the output enabled pin OUT_EN1 to supply power for the load input end of the ultraviolet sterilization circuit 40, and simultaneously conduct the triode Q5 through the LED1 pin of the main control chip U1. At this time, only the cover is closed, both the contact switch positive set 421 and the contact switch negative set 422 are conducted so that the whole series circuit shown in FIG. 8 can be connected. In this way, the ultraviolet LED 43 can be lit up to emit ultraviolet radiation to sterilize the nozzle of the electronic cigarette body.

As seen in FIG. 8, when the load 300 of the electronic cigarette body in the suction device is not connected with the ultraviolet sterilization circuit 40, none power supply is applied on the load input end of the ultraviolet sterilization circuit 40, and the transistor Q5 is shut off. At this time, closing the cover, that is, all the contacts of the contact switch positive set 421 and the contact switch negative set 422 are closed, but the whole ultraviolet sterilization circuit 40 is still unable to be conducted therefore, the ultraviolet LED 43 can't be lit up to sterilize the nozzle of the electronic cigarette body. The conduction of the entire ultraviolet sterilization circuit 40 must meet the following conditions: the load 300 is connected and the cover is closed, so, the ultraviolet sterilization circuit 40, the load input unit 30 and the load detection circuit 50 are to form an interlock control circuit to prevent users from being misoperation.

Referring back to FIG. 3, the load and sterilization combination control circuit 100 further includes a displaying screen 60 connected with the main control unit 10, and the battery management unit 20 is connected with the displaying screen 60 to apply power supply for the displaying screen 60.

Figure 9:
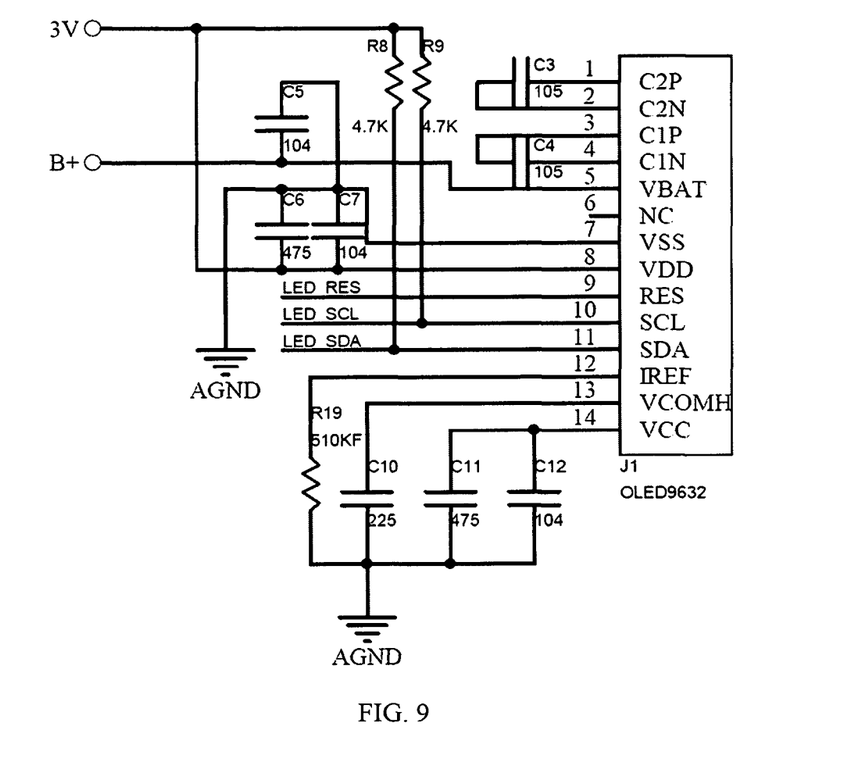
FIG. 9 is a schematic diagram of a displaying screen interface circuit of the load and sterilization combination control circuit of the present disclosure.

The displaying screen 60 of the present disclosure is mainly configured to display the working state of the entire suction device. The working state is represented that the main control unit 10 is communicated with the displaying screen 60 through a pin LED_RES a pin LED_SCL and a pin LED_SDA to send displaying instructions. Main displaying ways include a power display, a short-circuit protection, a low voltage protection, a charging status display, a battery power display and an ultraviolet lamp operating status display etc. FIG. 9 is shown a connection interface circuit of the displaying screen 60.

Referring to FIG. 3, the load 300 of the suction device of an embodiment of the present disclosure includes a heating wire 301, a suction control circuit 302 and a pneumatic induction switch 303. All the heating wire 301, the suction control circuit 302 and the pneumatic induction switch 303 are received in the electronic cigarette body. An input end of the suction control circuit 302 is connected with the output end of the load output unit 30, and an output end of the suction control circuit 302 is connected with the heating wire 301. The pneumatic induction switch 303 is electrically connected with the suction control circuit 302. The pneumatic induction switch 303 is configured to sense a suction action of the user and then transmit a signal to the suction control circuit 302, which can control the heating wire 301 for heating according to the signal.

The load and sterilization combination control circuit 100 of the present disclosure is provided the main control unit 10, the battery management unit 20, the load output unit 30, the load detection circuit 50 and the ultraviolet sterilization circuit 40, and the ultraviolet sterilization circuit 40 is set in linkage with the load detection circuit 50 and the load output unit 30. That is, when the load 300 of the suction device applied on the load output unit 30 is detected by the main control unit 10 via the load detection circuit 50, the load output unit 30 is turned on to supply power to the ultraviolet sterilization circuit 40 and to conduct the enabled switch 41 of the ultraviolet sterilization circuit 40. After that, the ultraviolet sterilization circuit 40 can be normally controlled by the operation switch 42 set thereon. That is, the ultraviolet sterilization circuit 40 can work normally only after the ultraviolet sterilization circuit 40 is connected with the load 300 of the suction device and the operation switch 42 is closed, which can avoid the waste of electric energy caused by misoperation. When the load 300 of the suction device is not applied on the load output unit 30, no external output is applied on the load output unit 30 and the enabled switch 41 of the ultraviolet sterilization circuit 40 isn't conducted. At this time, even if the operation switch 42 is closed, the ultraviolet sterilization circuit 40 can't work, or after the load 300 of the suction device is applied on the load output unit 30 if the operation switch 42 is not closed, the ultraviolet sterilization circuit 40 still can't work. Thus, it can avoid the waste of electric energy caused by misoperation.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A load and sterilization combination control circuit arranged on a suction device and comprising:

a main control unit, a battery management unit, a load output unit, a load detection circuit and an ultraviolet sterilization circuit;

an input end of the battery management unit connected with an external power supply, and an output end of the battery management unit connected with the main control unit and an input end of the load output unit so as to apply power supply for the main control unit, the load output unit, the load detection circuit and the ultraviolet sterilization circuit; the load output unit configured to output the power supply input from the battery management unit to the ultraviolet sterilization circuit and the load of the suction device; the load detection circuit connected between the battery management unit and the load of the suction device, and both the load output unit and the load detection circuit connected with the main control unit;

the ultraviolet sterilization circuit comprising an operation switch and an enabled switch connected with the operation switch in series, and connected with the main control unit;

the main control unit configured to conduct the load output unit and send an external output signal to the load output unit, and then conduct the enabled switch, when the load of the suction device applied on the load output unit is detected by the main control unit via the load detection circuit; and wherein the operation switch is configured to perform on-off control on the entire ultraviolet sterilization circuit after the enabled switch is turned on.

2. The load and sterilization combination control circuit as claimed in claim 1, wherein the load output unit comprises an enabled control circuit connected with the main control unit, and a boosted circuit; an input end of the enabled control circuit connected with the output end of the battery management unit, and an output end of the enabled control circuit connected with an input end of the boosted circuit; the boosted circuit comprising two output ends, with one output end thereof connecting with an input end of the ultraviolet sterilization circuit, and the other output end thereof connecting with the load of the suction device;

the ultraviolet sterilization circuit comprising the operation switch, an ultraviolet sterilization lamp and the enabled switch connected in series in turn;

the main control unit configured to controllably conduct the enabled control circuit and the enabled switch so as, to connect with the boosted circuit, when the load of the suction device applied on the load output unit is detected by the main control unit via the load detection circuit; and the operation switch configured to perform on-off control on the entire ultraviolet sterilization circuit to light up or turn, off the ultraviolet sterilization lamp after the enabled switch is turned on.

3. The load and sterilization combination control circuit as claimed in claim 1, wherein the battery management unit comprises a charging interface, a charging circuit connected with the charging interface, a battery, a battery protection circuit connected with both the charging circuit and the battery, and a voltage regulator circuit connected with the main control unit and configured to output a stable voltage to the main control unit, both the charging circuit and the battery protection circuit connected with the load output unit and the voltage regulator circuit;

the charging interface connected with the external power supply and configured to output an output voltage to the charging circuit, and then the charging circuit configured to charge the battery connected with the battery protection circuit, the battery protection circuit configured to output a voltage to the load output unit and the voltage regulator circuit.

4. The load and sterilization combination control circuit as claimed in claim 2, wherein the main control unit comprises a main control chip U1 comprising an output enabled pin OUT_EN1 connected with the enabled control circuit, an LED1 pin connected with the enabled switch and configured to control on and off of the enabled switch, and a load detection pin F_CHK connected with the load detection circuit.

5. The load and sterilization combination control circuit as claimed in claim 4, wherein the enabled control circuit comprises a field-effect tube Q1, a triode Q2 controllably connected with the field-effect tube Q1 and the output enabled pin OUT_EN1, the output end of the battery management unit connected with both the field-effect tube Q1 and the triode Q2;

the boosted circuit comprising a boosted chip U2 with an input end thereof connecting with the field-effect tube Q1, and an output end thereof connecting, with an ultraviolet output end VOUT and a load output end, the ultraviolet output end VOUT connected with the input end of the ultraviolet sterilization circuit; the load output end comprising a load anode contact point and a load cathode contact point connected with the ultraviolet output end VOUT in parallel, both the load anode contact point and the load cathode contact point conducted in series when the load is connected, and the load cathode contact point connected with the load detection circuit and then grounded.

6. The load and sterilization combination control circuit as claimed in claim 5, wherein the load output unit further comprises a voltage sampling circuit arranged at the output end of the boosted chip U2 and configured to sample a voltage to compare with a reference voltage of the boosted chip U2, and a short-circuit detection circuit connected with the load cathode contact point and a short-circuit detection pin CHA_CHK of the main control chip U1.

7. The load and sterilization combination control circuit as claimed in claim 6, wherein the main control chip U1 further comprises an enabled pin OUT_EN2 connected with the short-circuit detection circuit so as to control turn-on and turn-off of the short-circuit detection circuit.

8. The load and sterilization combination control circuit as claimed in claim 4, wherein the ultraviolet sterilization circuit further comprises a load input end, and a current-limiting resistance, and the operation switch comprises a contact switch positive set and a contact switch negative set; the ultraviolet lamp being an ultraviolet LED and the enabled switch being a triode Q5; all the load input end, the contact switch positive set, the ultraviolet LED, the contact switch negative set, the triode Q5 and the current-limiting resistance connected in series in turn to cooperatively form a series circuit thereof; and wherein The triode Q5 is controllably connected with the LED1 pin, and the contact switch positive set and the contact switch negative set are connected with or shut off the whole series circuit.

9. The load and sterilization combination control circuit as claimed in claim wherein the load and sterilization combination control circuit further comprises a displaying screen connected with the main control unit, and the battery management unit is connected with the displaying screen to apply power supply for the displaying screen.

10. The load and sterilization combination control circuit as claimed in claim 1, wherein the load of the suction device comprises a heating wire, a suction control circuit and a pneumatic induction switch electrically connected with the suction control circuit, an input end of the suction control circuit connected with an output end of the load output unit, and an output end of the suction control circuit connected with the heating wire.

11. The load and sterilization combination control circuit as claimed in claim 5, wherein the output end of battery management unit is connected with a second pin of the field-effect tube Q1 and is connected with a resistance R2; a first pin of the field-effect tube Q1 connected with a resistance R4, and then, together with the resistance R2, connected with a third pin of the triode Q2, a second pin of the triode Q2 being grounded, and the third pin of the triode Q2 connected in parallel with a resistance R6 and a resistance R7, an opposite end of the resistance R6 being grounded and an opposite end of the resistance R7 comprising a contact connected with the output enabled pin OUT_EN1 of the main control chip U1.

12. The load and sterilization combination control circuit as claimed in claim 11, wherein a third pin of the field effect tube Q1 is connected with a VCC pin of the boosted chip U2 for input, and also connected with an EN pin and an OC pin, of the boosted chip U2, an LX pin of the boosted chip U2 connected with the ultraviolet, output end VOUT and the load anode contact point through a diode D1, and the load cathode contact point connected with resistances R10, R11 in series and then grounded; an F_CHK contact arranged between the resistance R10 and the resistance R11 is connected with the load detection pin F_CHK of the main control chip U1.

13. The load and sterilization combination control circuit as claimed in claim 12, wherein the output end of the battery management unit is connected with a resistance R1 in parallel when the output end of the battery management unit is connected with the field-effect tube Q1 and the triode Q2; the resistance R1 connected with the load anode contact point; all the resistance R1, the load anode contact point, the load cathode contact point, the resistance R10, the load detection pin F_CHK and the resistance R11 cooperatively formed the load detection circuit.

14. The load and sterilization combination control circuit as claimed in claim 6, wherein the voltage sampling circuit comprises a resistance R3 connected in parallel with the ultraviolet output end VOUT and the load anode contact point, and a resistance R5 connected in series with the resistance R3; an FB pin of the boosted chip U2 connected between the resistance R3 and the resistance R5, a voltage first sampled by the resistance R3 and the resistance R5, and then compared with a voltage of an FB reference point of the boosted chip U2 so as to adjust the output voltage of the boosted chip U2.

15. The load and sterilization combination control circuit as claimed in, claim 14, wherein the short-circuit detection circuit comprises a field-effect tube Q3 and a resistance R17, a second pin of the field-effect tube Q3 connected with the resistance R15 and the resistance R17, an opposite end of the resistance R15 connected with a capacitor C9 and comprising a CHA_CHK contact connected with the short-circuit detection pin CHA_CHK of the main control chip U1, an opposite end of the resistance R17 being grounded, an opposite end of the capacitor C9 being grounded, and a third pin of the field-effect tube Q3 connected with the load cathode contact point.

16. The load and sterilization combination control circuit as claimed in claim 15, wherein a first pin of the field-effect tube Q3 is connected with a resistance R12, an opposite end of the resistance R12 comprising an OUT_EN2 contact connected with the enabled pin OUT_EN2 of the main control chip U1 when the main control chip U1 is configured conduct the field-effect tube Q3 through the enabled pin OUT_EN2, the short-circuit detection circuit is in a working state.

* * * * *